United States Patent [19]

Spatz

[11] Patent Number: 4,892,952
[45] Date of Patent: Jan. 9, 1990

[54] SUBSTITUTED HETEROARALKYL, HETEROARALKENYL OR HALOMETHYL FUNGICIDES

[75] Inventor: David M. Spatz, Fairfax, Calif.

[73] Assignee: Chevron Research Company, San Francisco, Calif.

[21] Appl. No.: 443,009

[22] Filed: Nov. 19, 1982

[51] Int. Cl.[4] .................. C07D 253/06; C07D 249/14; A01N 43/707; A01N 43/653

[52] U.S. Cl. .................... 514/245; 514/247; 514/255; 514/272; 514/392; 514/404; 548/255; 548/269; 548/262; 548/300; 548/341; 548/342; 548/352; 548/353; 548/356; 548/378; 544/182; 544/215; 544/216; 544/224; 544/335

[58] Field of Search ............... 548/255, 269, 262, 300, 548/341, 342, 352, 353, 356, 378; 544/182, 215, 216, 224, 335; 424/249, 250, 251, 269, 273 R, 273 P; 514/245, 255, 272, 247, 392, 404

[56] References Cited

U.S. PATENT DOCUMENTS 4,079,143 3/1978 Balasubramanyan et al. ...... 424/269
4,080,462 3/1978 Brookes et al. ................. 424/273 R

FOREIGN PATENT DOCUMENTS 56-152446 11/1981 Japan .

Primary Examiner—Mary C. Lee
Assistant Examiner—John A. H. Russell
Attorney, Agent, or Firm—T. G. DeJonghe; R. C. Gaffney

[57] ABSTRACT

Compounds of the formula:

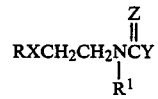

wherein R is phenyl or phenyl substituted with 1 to 4 of the same or different substituents selected from fluoro, chloro, bromo, iodo, lower alkyl and trihalomethyl;
$R^1$ is lower alkyl;
Y is lower alkenyl substituted with a 5- or 6-member heterocyclic ring containing 1 to 3 nitrogen atoms and the remainder of the ring atoms carbon atoms, or —CH$_2$W wherein W is fluoro, chloro, bromo, iodo, or a 5- to 6-member heterocyclic ring containing 1 to 3 nitrogen atoms and the remainder of the ring atoms carbon atoms; and
X and Z are independently sulfur or oxygen; are effective fungicides.

17 Claims, No Drawings

SUBSTITUTED HETEROARALKYL, HETEROARALKENYL OR HALOMETHYL FUNGICIDES

BACKGROUND OF THE INVENTION

This invention is drawn to novel fungicides.

With the world more dependent for food on an ever decreasing amount of cultivated farmland, it is increasingly important to develop effective fungicides which protect crops from fungicidal destruction.

Kozlik et al, in CA 79:53327Z, disclosed 1carbamoylimidazoles as insecticidal.

Brookes et al, in U.S. Pat. Nos. 4,080,462 and 3,991,071, disclosed 1-(N,N-disubstituted carbamoyl and thiocarbamoyl)-imidazoles as fungicidal.

SUMMARY OF THE INVENTION

The compounds of the present invention are represented by the formula:

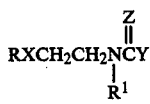

wherein R is phenyl, or phenyl substituted with 1 to 4 substituents independently selected from fluoro, chloro, bromo, iodo, lower alkyl, and trihalomethyl;

$R^1$ is lower alkyl;

Y is lower alkenyl substituted with a 5- or 6-member heterocyclic ring containing 1 to 3 nitrogen atoms and the remainder of the ring atoms carbon atoms, or —CH2W wherein W is fluoro, chloro, bromo, iodo, or a 5- or 6-member heterocyclic ring containing 1 to 3 nitrogen atoms and the remainder of the ring atoms carbon atoms;

Z is oxygen, or sulfur; and

X is oxygen, or sulfur.

Among other factors, the present invention is based on my finding that the compounds of this invention are effective fungicides. In particular, some of the compounds of this invention possess good activity against Bean Powdery Mildew.

In part due to their superior fungicidal activity, preferred R groups include phenyl substituted with 1 to 3 halogens. Particularly preferred R groups are 2,4,6-trihalophenyl and 2,6-dihalophenyl.

Preferred halogens include chloro and bromo.

Preferred lower alkyl $R^1$ groups include, for instance, methyl, ethyl, and n-propyl. Particularly preferred $R^1$ groups are n-propyl and ethyl.

Preferred Y groups include, for instance, the halomethyl groups, vinyl substituted with a 5- or 6-member heterocyclic ring containing 1 to 2 nitrogen atoms and the remainder of the ring atoms carbon atoms.

Definitions

As used herein, the following terms have the following meanings, unless expressly stated to the contrary.

The term "alkenyl" refers to unsaturated alkyl groups having a double bond [e.g., $CH_3CH=CH(CH_2)_2—$,-] and includes both straight- and branched-chain alkenyl groups.

"Lower alkenyl" groups refer to alkenyl groups having from 2 through 6 carbon atoms. Typical lower alkenyl groups include, for example, ethylene, but-3-enyl, hex-4-enyl, 2-methylpent-4-enyl, and the like.

The term "alkyl" refers to both straight- and branched-chain alkyl groups. Generally, such alkyl groups contain from 1 through 12 carbon atoms.

The term "lower alkyl" refers to both straight and branched-chain alkyl groups having a total from 1 through 6 carbon atoms and includes primary, secondary and tertiary alkyl groups. Typical lower alkyls include, for example, methyl, ethyl, n-propyl, isopropyl, n-butyl, t-butyl, n-hexyl, and the like.

The term "halo" or "halogen atom" refers to the groups fluoro, chloro, bromo and iodo.

The term "a 6-member heterocyclic ring containing 1 to 3 nitrogen atoms" refers to the groups pyridyl, pyridazinyl, pyrimidyl, pyrazinyl, triazinyl, and the like. The term "a 5-member heterocyclic ring containing 1 to 3 nitrogen atoms" refers to the groups imidazolyl, pyrrolyl, pyrazolyl, triazolyl, and the like. The term "a heterocycle containing a free nitrogen" refers to those heterocycles in which the nitrogen of the heterocycle is bonded with a hydrogen and includes, for instance, pyrrole

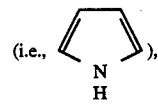

1,2,4-triazole

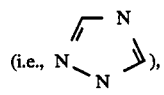

midazole

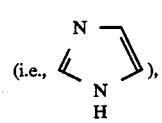

pyrazole

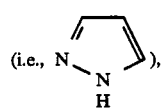

and the like.

The term "heteroaralkyl" refers to a lower alkyl group substituted with a 5- or 6-member heterocyclic ring containing 1 to 3 nitrogen atoms, and refers to the groups 1-methyl-1,2,4-triazolyl, 3-picolyl, and the like.

The term "heteroaralkenyl" refers to a lower alkenyl group substituted with a 5- or 6-member heterocyclic ring containing 1 to 3 nitrogen atoms, and refers to the groups 2-(3-pyridyl)vinyl, 2-(5-pyrimidyl)vinyl, and the like.

DETAILED DESCRIPTION OF THE INVENTION

The compounds of the present invention are conveniently prepared according to the following synthetic scheme:

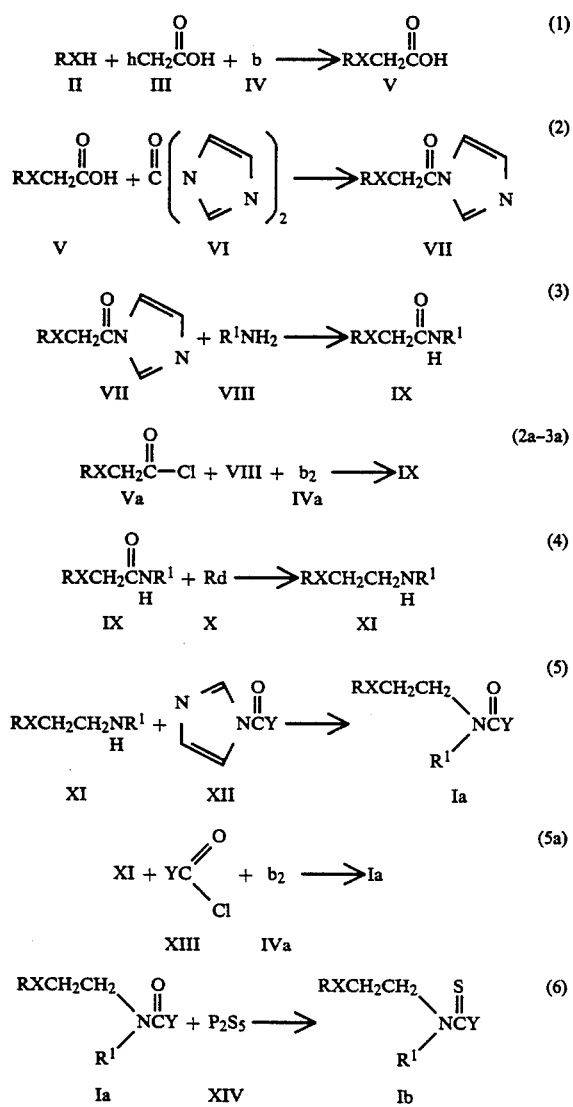

wherein R, R¹, Y and X are as defined above;
Rd is a reducing agent;
h is a halogen atom;
b is a base; and
b₂ is an acid scavenger (base).

Reaction (1) is conducted by adding approximately 2 equivalents of a base, IV, to II. The reaction is done in the liquid phase employing an organic solvent such as ethanol, methanol, and the like, or, alternatively, water. Preferably, the base employed is an inorganic base. Suitable inorganic bases include, for instance, sodium hydride, sodium methoxide, metallic sodium, and the like. After addition of IV, an approximately equimolar amount of α-haloacetic acid, III, is added to the system. Reaction pressure is not critical and for convenience, the reaction is generally conducted at atmospheric pressure. The reaction is generally conducted at from 0° C to 100° C, although preferably at from 40° C to 70° C, and is generally complete from within 1 to 48 hours. The resulting intermediate, V, is isolated by conventional procedures such as extraction, filtration, chromatography, distillation, or alternatively, used in Reaction (2) without purification and/or isolation.

Reaction (2) is conducted by adding an essentially equimolar amount of carbonyldiimidazole, VI, to V. The reaction is conducted in the liquid phase using an inert anhydrous organic solvent such as chloroform, methylene chloride, dimethoxyethane, toluene, and the like. Reaction pressure is not critical and for convenience, the reaction is generally conducted at atmospheric pressure. The reaction is generally conducted at from 0° C. to 100° C., although preferably at room temperature, and is generally complete from within 1 to 24 hours. The resulting carboxylic acid imidazolide, VII, may be isolated by conventional procedures such as extraction, filtration, chromatography, distillation, and the like. Alternatively and preferably the resulting intermediate is not isolated from the reaction solution but is used directly in Reaction (3).

Reaction (3) is conducted by adding an essentially equimolar amount of the appropriate primary amine, VIII, to VII. The reaction is conducted in the liquid phase using an inert anhydrous organic solvent such as chloroform, methylene chloride, dimethoxyethane, toluene, and the like. Preferably, the reaction solution is the same as was employed in Reaction (2) with the appropriate amine, VIII, merely added to the system after completion of Reaction (2). Reaction pressure is not critical and for convenience, the reaction i generally conducted at atmospheric pressure. The reaction is generally conducted at from 0° C. to 100° C., although preferably at room temperature, and is generally complete from within 1 to 24 hours. The resulting amide, IX, is isolated by conventional procedures such as extraction, filtration, chromatography, distillation, or alternatively, used in Reaction (4) without purification and/or isolation.

Alternatively, IX may be prepared according to Reaction (2a–3a) by adding a solution of the acid chloride corresponding to V to a solution of VIII. The acid chloride Va is prepared from the acid V by techniques known to reaction is conducted in the presence of b₂ (IVa), an acid scavenger such as triethylamine, pyridine, an alkylamine, sodium carbonate, or the like. The reaction is conducted in the liquid phase using an inert organic solvent such as methylene chloride, chloroform, dioxane, toluene, and the like. The reaction is carried out at a temperature of about −50° C. to about 100° C., preferably from about 0° C. to about 25° C. After the addition is complete, the reaction mixture is allowed to return to room temperature. The reaction is generally complete within about 0 to about 48 hours after the addition is complete. The resulting amide IX is isolated by conventional procedures such as extraction, filtration, chromatography, distillation, or alternatively used in Reaction (4) without further purification or isolation.

Reaction (4) is a conventional reduction of the amide to the amine. The reaction is conducted by adding an essentially equimolar amount of a reducing agent, Rd, to IX. The reaction is conducted in the liquid phase employing an inert anhydrous organic solvent such as toluene, benzene, tetrahydrofuran, and the like. Suitable reducing agents include, for instance, lithium aluminum hydride, borane, borane methyl sulfide, and the like.

Preferably, due to the ease in handling the reagent, borane methyl sulfide is employed as the reducing agent. Reaction pressure is not critical and for convenience, the reaction is conducted at atmospheric pressure. The reaction is generally conducted at from 0° C to 110° C, although preferably at from 30° C to 70° C, and is generally complete from within 1 to 24 hours. The resulting amine, XI, is isolated by conventional procedures such as extraction, filtration, chromatography, distillation, or alternatively, used in Reaction (5) without purification and/or isolation.

Reaction (5) is conducted by first preparing reagent XII. XII is prepared by adding an essentially equimolar amount of carbonyldiimidazole to the appropriate acid, $YCO_2H$ wherein Y is as defined above. The reaction is conducted in the liquid phase using an inert anhydrous organic solvent such as chloroform, methylene chloride, dimethoxyethane, toluene, and the like. Reaction pressure is not critical and for convenience, the reaction is generally conducted at atmospheric pressure. The reaction is generally conducted at from 0° C to 100° C, although preferably at room temperature, and is generally complete from within 1 to 24 hours. The resulting reagent, XII, may be isolated by conventional procedures such as extraction, filtration, chromatography, distillation, and the like. Alternatively and preferably, the reagent is not isolated from the reaction solution but an essentially equimolar amount of the amine, XI, is added to the system. Reaction pressure for this reaction is not critical and for convenience, the reaction is generally conducted at atmospheric pressure. After addition of XI, the reaction is generally conducted at room temperature and is generally complete from within 1 to 24 hours. The product, Ia, is then isolated by conventional procedures such as extraction, filtration, chromatography, and distillation.

Alternatively, product Ia may be prepared by Reaction (5a) using the acid chloride XIII corresponding to $YCO_2H$. Acid chloride XIII may be conveniently prepared by combining approximately equimolar amounts of $YCO_2H$ and thionyl chloride. The reaction is conducted in the liquid phase using an inert organic solvent such as methylene chloride, toluene, chloroform, and the like. It is preferred to conduct the reaction in the presence of a catalytic amount of dimethylformamide. The reaction mixture is heated to reflux and refluxed for about 0 to about 24 hours. The mixture is stirred until gas evolution ceases. After the temperature of the mixture returns to room temperature, XIII may be used in Reaction (5a) without purification or isolation. Since XIII is susceptible to hydrolysis, minimal handling of it is preferred.

Reaction (5a) is conducted by combining XIII, with XI and IVa. The reaction is conducted in the liquid phase using an inert organic solvent such as methylene chloride, chloroform, toluene and the like. Suitable acid scavengers, $b_2$ (IVa), include bases such as triethylamine, pyridine, an alkylamine, sodium carbonate, and the like. The reaction is carried out at a temperature of about $-25°$ C. to about 100° C., preferably from about 0° C. to about 25° C., and may be conveniently carried out at room temperature. The reaction is generally complete within about 0 to about 24 hours. Product Ia is then isolated by conventional procedures such as extraction, filtration, chromatography, distillation, or alternatively, used in Reaction (6) without purification and/or isolation.

Reaction (6) is conducted by adding an essentially equimolar amount of phosphorus pentasulfide, XIV, to Ia. The reaction is conducted in the liquid phase using an inert anhydrous organic solvent such as toluene, tetrahydrofuran, and the like. Preferably, the system is exposed to microwave radiation in order to facilitate the dispersion of phosphorus pentasulfide into solution. Reaction pressure is not critical and for convenience, the reaction is generally conducted at atmospheric pressure. The reaction is generally conducted at from 15° C. to 100° C., although preferably it is conducted at the ambient temperature and is generally complete from within 1 to 48 hours. The product Ib is then isolated by conventional procedures such as extraction, filtration, chromatography, distillation, and the like.

Alternatively, the halomethyl Y substituents of this invention are preferably prepared from the starting amine, XI, according to the following synthetic scheme:

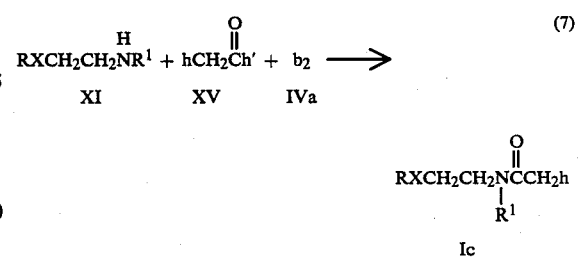

wherein $b_2$, X, R and $R^1$ are as defined above; and h and h' are independently halogen.

Reaction (7) is conducted by adding an essentially equimolar amount of an α-haloacetyl halide, XV, to XI. The reaction is conducted in the liquid phase employing an anhydrous aprotic organic solvent such as chloroform, methylene chloride, toluene, and the like. An essentially equimolar amount of a base, $b_2$, is added to the reaction to scavenge the acid generated. Preferably, $b_2$ is a base such as a trialkylamine (e.g., triethylamine), pyridine, sodium carbonate, or the like. Reaction pressure is not critical and for convenience, the reaction is generally conducted at atmospheric pressure. The reaction is generally conducted at from 0° C. to 100° C., although preferably at from 15° C. to 40° C., and is generally complete within 1 to 48 hours. The product is then isolated by conventional procedures such as extraction, filtration, chromatography, distillation, and the like.

The halomethyl compounds prepared in accordance with Reaction (7) may be utilized as convenient starting materials for reaction with 1,2,4-triazoles (although any heterocycle containing a free nitrogen may be employed in lieu of the 1,2,4-triazole), to produce the 1-(1,2,4triazolyl)methyl substituents as depicted in Reaction (8) below:

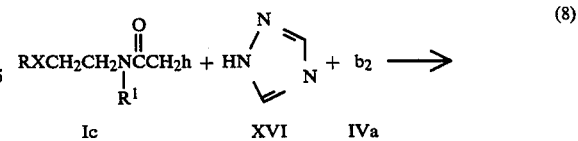

-continued

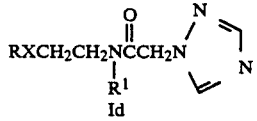

wherein $b_2$, X, R, $R^1$, and h are as defined above.

Reaction (8) is conducted by adding an essentially equimolar amount of 1,2,4-triazole XVI to Ic. The reaction is conducted in the liquid phase employing an anhydrous aprotic organic solvent such as acetonitrile, toluene, dioxane, and the like. An essentially equimolar amount of a base, $b_2$, is optionally added to the reaction to scavenge the acid generated. Preferably, $b_2$ is a base such as pyridine, triethylamine, sodium carbonate, and the like. Reaction pressure is not critical and for convenience, the reaction is generally conducted at atmospheric pressure The reaction is generally conducted at from 20° C. to 110° C., although preferably at 70° C. to 100° C., and is generally complete within 1 to 48 hours. The product Id is then isolated by conventional procedures such as extraction, filtration, chromatography, distillation, and the like.

Utility

The compounds of the invention are effective in controlling fungal infections. Some of the compounds of this invention are particularly effective in controlling powdery mildew infections caused by the organism *Erysiphe polygoni*. Some of the compounds of this invention are also useful for controlling leaf blights caused by organisms such as *Phytophthora infestans conidia*, *Alternaria solani conidia*, and *Septoria apii*. In addition, some of the compounds of this invention are also useful for controlling fungal infections caused by organisms such as *Uromyces phaseoli tipica*, *Plasmopara viticola*, and *Piricularia oryzae*. However, some fungicidal compounds of this invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperature ranges refer to the Centigrade system and the term "ambient" or "room temperature" refers to about 20° C. to 25° C. The term "percent" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

Compounds which were prepared in accordance with Examples 1 through 18 below are found in Tables I and II.

EXAMPLES

Example 1

Preparation of 2,4,6-trichlorophenoxyacetic acid 2,4,6-trichlorophenol, 100.7 gm, was added to 250 ml of ethanol. 228.6 ml of a 25% solution of sodium methoxide (2 equivalents) in methanol was then added to the system. The system was stirred at room temperature for approximately 1 hour. Afterwards, 69.5 gm of bromoacetic acid was added and the system then heated to reflux. After 18 hours, an additional equivalent of sodium methoxide in methanol (114.3 ml) was added as well as 34.7 gm of bromoacetic acid. The system was continued at reflux for 12 hours. The reaction was then stopped and the solvent removed by stripping. The resulting solid was washed with water and then with ether. Concentrated HCl was next added to the solid and the system was left standing for 12 hours. Afterwards, the product was filtered, washed with water and air dried. Toluene was then added to the product. The toluene was removed by stripping and any remaining water was azeotroped off with the toluene. 74.4 gm of 2,4,6-trichlorophenoxyacetic acid was recovered.

Example 2

Preparation of N-(n-propyl)-2,4,6-trichlorophenoxyacetamide

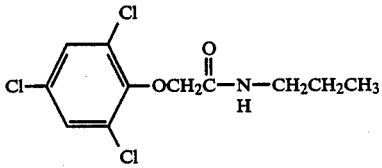

(a) 2,4,6-trichlorophenoxyacetic acid, 47.5 gm, was added to 300 ml of methylene chloride along with 30.3 gm of carbonyldiimidazole. The system was stirred overnight to give the carboxylic acid imidazolide.

(b) 15.4 ml of n-propylamine was then added to the system. The system was then stirred at room temperature for an additional 20 hours. The reaction was stopped and the organic solution was washed first with a dilute HCl solution, then with a sodium bicarbonate solution and then with water. The methylene chloride was removed by stripping to give the N-(n-propyl)-2,4,6-trichlorophenoxyacetamide.

Example 2a

Preparation of N-(n-propyl)-2,4,6-trichlorophenoxyacetamide

A solution of 2625 gm (9.62 moles) 2,4,6trichlorophenoxyacetic acid chloride in methylene chloride (total solution weight 5403 gm) was added to a solution of 1251 gm (21.17 moles) n-propylamine in 7.6 l methylene chloride in a 22-liter flask over a period of 2 hours. During the addition, the temperature of the system was maintained at about 5° C to 7° C using a dry ice/isopropyl alcohol bath. During the addition, some white solids precipitated. After the addition was complete, the cooling bath was removed allowing the temperature of the system to rise to 10° C over 25 minutes. The system temperature was then raised to 23° C over 10 minutes by use of a warm water bath. Sample NMR and IR spectra indicate the reaction was complete. After removal of the warming bath, the methylene chloride solution was washed 3 times with 4 l water. The aqueous layer and organic layers were separated and the organic phase was dried over 150 gm magnesium sulfate. The organic solution was stripped until the weight reached about 3 kg. While the system was still in the hot water bath, 3.5 l hexane was added, giving a clear solution. The system was then cooled to 20° C., giving a very thick slurry of crystals. The crystals were filtered and washed with 2 l hexane. Air drying gave 2102 gm.

The mother liquor and hexane washings were stripped to give 450 gm of a brown oil which solidified upon cooling. Recrystallization from hexane (about 900 ml), followed by filtering the crystals, washing the crystals with hexane (about 500 ml), and air drying gave an additional 342 gm of the product.

Example 3

Preparation of N-(n-propyl) ethalamine 2,4,6-trichlorophenylether

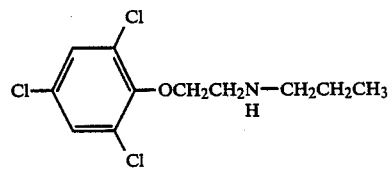

N-(n-propyl)-2,4,6-trichlorophenoxyacetamide, 44.0 gm, was added to 250 ml of toluene. 28 ml of borane methyl sulfide [BH$_3$ (CH$_3$)$_2$S](2 equivalents) was then slowly added to the system. The system was heated at approximately 60° C. for 15 hours at which time reaction completion was checked by IR spectroscopy. 200 ml of methanol was then slowly added to the system. After addition of the methanol, the system was acidified by bubbling in HCl gas. Afterwards, the system was refluxed for 1 hour. The solvent was then removed by stripping. The resulting oil was dissolved in methanol which was then stripped. The oil was next dissolved in methylene chloride. The organic solution was washed with a sodium hydroxide solution and then with water. The methylene chloride was removed by stripping to give 36.3 gm of the N-(n-propyl) ethanolamine 2,4,6-trichlorophenylether, as a yellow oil.

Example 4

Preparation of N-(α-bromoacetyl), N-(n-propyl), ethanolamine 2,4,6-trichlorophenylether

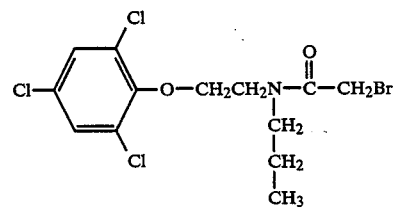

N-(n-propyl) ethanolamine 2,4,6-trichlorophenylether, 11.3 gm, was added to 100 ml of methylene chloride. 5.6 ml of triethylamine was added to the system. The system was stirred at about −70° C for 5 minutes and then 3.5 ml of α-bromoacetyl bromide was added dropwise. The system was stirred at room temperature for an additional 18 hours. The reaction was stopped and the system poured into 100 ml of water. The product was extracted with methylene chloride. The organic solution was dried over magnesium sulfate and the methylene chloride was then removed by stripping to give the N-(α-bromoacetyl), N-(npropyl) ethanolamine 2,4,6-trichlorophenylether as a brown oil. Listed as Compound No. 3 in Table I.

Example 5

Preparation of N-(α-[1-(1,2,4-triazolyl)]acetyl, N-(n-propyl) ethanolamine 2,4,6-trichlorophenylether

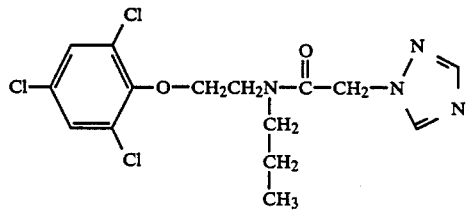

To a hot solution (about 60° C to about 80° C) of 3.6 gm potassium carbonate and 5.4 gm 1,2,4-triazole in 150 ml acetonitrile, 10.5 gm N-(α-bromoacetyl), N-(n-propyl) ethanolamine 2,4,6-trichlorophenylether, the product of Example 4, was added. The system was heated to reflux and maintained at reflux for 18 hours. The reaction mixture was then cooled and filtered; and the filtrate was stripped. The residue from the filtrate was dissolved in methylene chloride and washed twice with a saturated brine solution. The methylene chloride was stripped; the residue was then triturated with hexane to give the desired product. Listed as Compound No. 1 in Table I Example 6

Preparation of N-(α-bromothioacetyl), N-(n-propyl) ethanolamine 2,4,6-trichlorophenylether

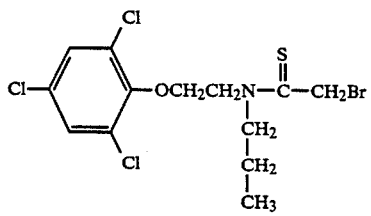

To 200 ml tetrahydrofuran, 4.02 gm N-(α-bromoacetyl), N-(n-propyl) ethanolamine 2,4,6-trichloro-phenylether, the product of Example 4, is added. Phosphorus pentasulfide, $P_2S_5$, 23.0 gm, is added to the system. The resulting reaction mixture is exposed to microwave radiation and stirred there for 2 hours. The system is then filtered and the solvent is removed by stripping to give the desired product.

Example 7

Preparation of N-(n-propyl), N-[β-(3-pyridyl)acrylyl]ethanolamine 2,4,6-trichlorophenYlether

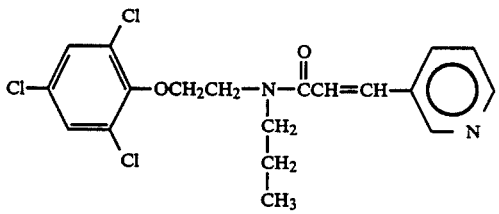

(a) β-(3-pyridyl) acrylic acid, 2.2 gm, was added to 50 ml of methylene chloride. 2.4 gm of carbonyldiimidazole was added to the system. The system was stirred at room temperature for 18 hours to give the β-(3-pyridyl) acrylic acid imidazolide.

(b) N-(n-propyl) ethanolamine 2,4,6-dichlorophenylether, the product of Example 3, 5.2 gm, was then added to the system. The system was stirred at room temperature for 72 hours. The reaction was then stopped and the methylene chloride solution washed first with a sodium bicarbonate solution and then with water. The methylene chloride solution was dried over magnesium sulfate and the methylene chloride removed by stripping to give a residue which was chromatographed to give 1.6 gm of the N-(n-propyl), N-[β-(3-pyridyl)acrylyl]ethanolamine 2,4,6-trichlorophenylether. Listed as Compound No. 2 in Table I.

Example 8

Preparation of N-(n-propyl), N-[α-(3-pyridyl)acetyl]ethanolamine 2,4,6-trichlorophenylether

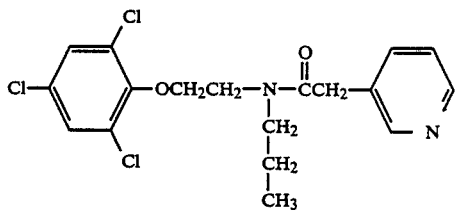

(a) α-(3-pyridyl)acetic acid, 6.8 gm, was added to 100 ml of methylene chloride. 8.1 gm of carbonyldiimidazole was added to the system. The system was stirred at room temperature for 5 hours to give the α-(3-pyridyl)acetic acid imidazolide.

(b) N-(n-propyl) ethanolamine 2,4,6-trichlorophenylether, the product of Example 3, 15.9 gm, was then added to the system. The system was stirred at room temperature for 16 hours. The reaction was then stopped and the methylene chloride solution was washed first with a sodium bicarbonate solution and then with water. The methylene chloride solution was dried over magnesium sulfate and the methylene chloride removed by stripping to give the desired product. Listed as Compound No. 4 in Table I.

Example 9

Preparation of 2,6-dichlorothiophenoxyacetic acid 2,6-dichlorothiophenol, 50.0 gm, was added to 50 ml of ethanol. 63.8 ml of a 25% solution of sodium methoxide (2 equivalents) in methanol was then added to the system. The system was stirred at room temperature for approximately 3 hours. Afterwards, 20 ml of bromoacetic acid was added and the system then heated to reflux. The system was continued at reflux for 16 hours. The reaction was then stopped and the solvent removed by stripping. The resulting material was dissolved with basic aqueous solution water and then washed with methylene chloride. Concentrated HCl was next added to the aqueous solution to acidify it. The product was extracted with methylene chloride. The methylene chloride solution was stripped and triturated with hexane. The product was then filtered, washed with water and air dried to yield 55.3 gm of the 2,6-dichlorothiophenoxyacetic acid.

Example 10

Preparation of N-(n-propyl)-2,6-dichlorothiophenoxyacetamide (a) 2,6-dichlorothiophenoxyacetic acid, the product of Example 9, 55.3 gm, was added to 250 ml of methylene chloride along with 37.8 gm of carbonyldiimidazole. The system was stirred overnight at room temperature to give the carboxylic acid imidazolide.

(b) 19.1 ml of n-propylamine was then added to the system. The system was then stirred at room temperature for an additional 65 hours. The reaction was stopped and the organic solution was washed first with a dilute HCl solution, then with a sodium bicarbonate solution and then with water. The methylene chloride was removed by stripping to give 33.7 gm of the N-(n-propyl)-2,6-dichlorothiophenoxyacetamide.

Example 11

Preparation of N-(n-propyl) 2-aminoethanethiol 2,6-dichlorophenylthioether

N-(n-propyl)-2,6-dichlorothiophenoxyacetamide, the product of Example 10, 33.7 gm, was added to 250 ml of tetrahydrofuran. 34.4 ml of borane methyl sulfide (3 equivalents) was then slowly added to the system. The system was heated at approximately 55° C for 18 hours at which time reaction completion was checked by IR spectroscopy. 200 ml of methanol was then slowly added to the system. After addition of the methanol, the system was acidified by bubbling in HCl gas. Afterwards, the system was refluxed for 1 hour. The solvent was then removed by stripping. The resulting oil was dissolved in methanol which was then stripped. The oil was next dissolved in methylene chloride. The methylene chloride solution was washed with a sodium hydroxide solution and then with water. The methylene chloride was removed by stripping to give 28.2 gm of the N-(n-propyl) 2-aminoethanethiol 2,6-dichlorophenylthioether.

Example 12

Preparation of N-(n-propyl), N-(α-chloroacetyl)-2-aminoethanethiol 2,6-dichlorophenylthioether

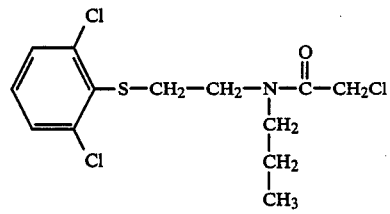

N-(n-propyl)-2-aminoethanethiol 2,6-dichlorophenylthioether, 26.4 gm, is added to 100 ml of methylene chloride. 11 gm of triethylamine is added to the system. The system is stirred at room temperature for 5 minutes and then 11.3 gm of α-chloroacetyl chloride is added. The system is then stirred at room temperature for a 16 hours. The reaction is stopped and the system poured into 200 ml water. The product is extracted with methylene chloride. The methylene chloride solution is dried over magnesium sulfate and the methylene chloride is removed by stripping to give the desired product.

Example 13

Preparation of N-ethyl-2,4,6-trichlorophenoxyacetamide

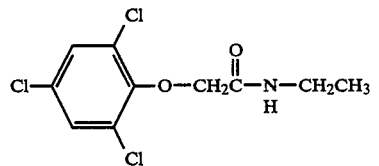

(a) 2,4,6-trichlorophenoxyacetic acid, the product of Example 1, 16.5 gm, was added to 150 ml of methylene chloride along with 10.5 gm of carbonyldiimidazole. The system was stirred overnight to give the 2,4,6trichlorophenoxyacetic acid imidazolide.

(b) Excess ethylamine was bubbled into the imidazolide solution from Step (a). The system was then stirred at room temperature for an additional 24 hours. The reaction was stopped and the organic solution was washed first with a dilute HCl solution, then with a sodium bicarbonate solution, and then with water. The methylene chloride was removed by stripping to give the desired product.

Example 14

Preparation of N-ethyl ethanolamine 2,4,6-trichlorophenylether

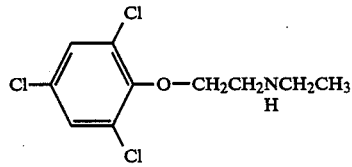

N-ethyl-2,4,6-trichlorophenoxyacetamide, the product of Example 13, 10.5 gm, was added to 80 ml of toluene. 7.0 ml of borane methyl sulfide

[BH$_3$(CH$_3$)$_2$S](2 equivalents) was then slowly added to the system. The system was heated at approximately 60° C for 18 hours at which time reaction completion was checked by IR spectroscopy. 50 ml of methanol was then slowly added to the system. After addition of the methanol, the system was acidified by bubbling in HCl gas. Afterwards, the system was refluxed for 1 hour. The solvent was removed by stripping. The resulting oil was dissolved in methanol which was then stripped. The oil was next dissolved in methylene chloride and the methylene chloride solution was washed with a sodium hydroxide solution and then with water. The methylene chloride was removed by stripping to give 10.0 gm of the N-ethyl ethanolamine 2,4,6-trichlorophenylether.

By reacting with the appropriate reagents, the following compounds are prepared from the N-ethyl ethanol-amine amine 2,4,6-trichlorophenylether:

N-(α-bromoacetyl), N-ethyl ethanolamine 2,4,6-trichlorophenylether;

N-(α-chloroacetyl), N-ethyl ethanolamine 2,4,6-trichlorophenylether;

N-[α-(3-pyridyl)acetyl], N-ethyl ethanolamine 2,4,6-trichlorophenylether; and

N-ethyl, N-[β-(3-pyridyl)acrylyl]ethanolamine 2,4,6-trichlorophenylether.

Example 15

Preparation of 4-t-butylphenoxyacetic acid

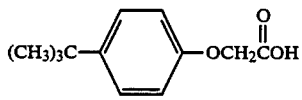

4-t-butylphenol, 37.5 gm, was added to 300 ml of ethanol. 57.2 gm of a 25% solution of sodium methoxide (2 equivalents) in methanol was then added to the system. The system was stirred at room temperature for approximately 0.5 hour. Afterwards, 29.5 ml of bromoacetic acid was added and the system was then heated to reflux for 18 hours. The reaction was then stopped and the solvent removed by stripping. The resulting solid was dissolved in methylene chloride; dilute sodium hydroxide was added to give a basic pH. The resulting precipitate was dissolved in hydrochloric acid and then extracted wit methylene chloride. The methylene chloride was then stripped, and the resulting crude product air dried. Toluene was then added to the product. The toluene was removed by stripping and any remaining water was azeotroped off with the toluene to give 33.3 gm of 4-t-butylphenoxyacetic acid.

Example 16

Preparation of N-(n-propyl)-4-t-butylphenoxyace

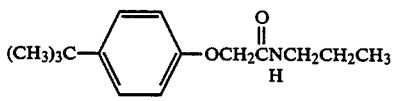

(a) 4-t-butylphenoxyacetic acid, the product of Example 15, 33.3 gm, was added to 300 ml of methlene chloride along with 26.4 gm of carbonyldiimidazole. The system was stirred overnight to give the 4-t-butyl-phenoxyacetic acid imidazolide.

(b) 13.4 ml of n-propylamine was then added to the system. The system was then stirred at room temperature for an additional 24 hours. The reaction was stopped and the organic solution was washed first with a dilute HCl solution, then with a sodium bicarbonate solution, and then with water. The methylene chloride was removed by stripping to give the N-(n-propyl)-4-t-butylphenoxyacetamide.

Example 17

Preparation of N-(n-propyl) ethanolamine 4-t-butylphenylether

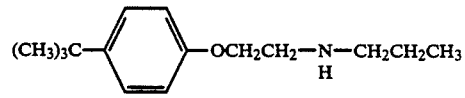

To 250 ml of a 1:1 mixture of toluene: tetrahydrofuran, 35.0 gm N-(n-propyl)-4-t-butylphenoxy-acetamide, the product of Example 16, was added. The resulting mixture was heated to reflux and then 42.8 ml borane methylsulfide was added slowly. The reaction mixture was maintained at reflux for 48 hours at which time completion of the reaction was checked by IR spectroscopy. The reaction mixture was then cooled and 200 ml methanol was added slowly to the system. The system was then acidified by bubbling hydrogen chloride gas through it, and then heated to reflux and refluxed for 1 hour. The solvent was removed by stripping; the resulting oil was redissolved in methanol and the methanol stripped. The residue was dissolved in methylene chloride and basified with sodium hydroxide. The methylene chloride solution was then washed with water. The methylene chloride was stripped to give 31.2 gm of the N-(n-propyl) ethanolamine 4-t-butylphenylether.

Example 18

Preparation of N-(n-propyl), N-(α-chloroacetyl) ethanolamine 4-t-butYlphenYlether

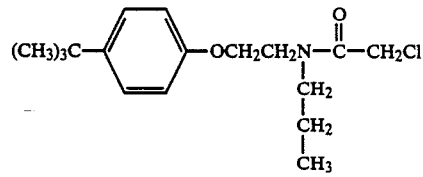

N-(n-propyl) ethanolamine 4-t-butylphenylether, 23.3 gm, is added to 100 ml of methylene chloride. 11 gm of triethylamine is added to the system. The system is stirred at room temperature for 5 minutes and then 11.3 gm of α-chloroacetyl chloride is added. The system is then stirred at room temperature for 16 hours. The reaction is stopped and the system was poured into 200 ml of water. The product is extracted with methylene chloride solution. The methylene chloride solution is dried over magnesium sulfate and the methylene chloride is removed by stripping to give the desired product.

Other compounds which are prepared in accordance with Examples 1 to 18 above include, for instance:

N-(n-propyl), N-(α-chloroacetyl) ethanolamine 4-methylphenylether;

N-(n-propyl), N-(α-chloroacetyl) 2-aminoethanethiol 4-methylphenylthioether;

N-(n-propyl), N-(α-bromoacetyl) ethanolamine 4-trifluoromethylphenylether;

N-(n-propyl), N-(α-bromoacetyl) 2-aminoethanethiol 4-trifluoromethylphenylthioether;
N-ethyl, N-(α-iodoacetyl) 2-aminoethanethiol 2,4,6-ribromophenylthioether;
N-ethyl, N-(α-iodoacetyl) ethanolamine 4,6-tribromophenylether,
N-(n-hexyl), N-[α-(3-pyridyl)acetyl]ethanolamine 2,6-dichlorophenylether;
N-(n-hexyl), N-[α-(3-pyridyl)acetyl]2-aminoethanethiol 2,6-dichlorophenylthioether;
N-ethyl, N-[α-(3-pyridyl)acetyl]ethanolamine 2,6-dichlorophenylether;
N-ethyl, N-[α-(3-pyridyl)acetyl]2-aminoethanethiol 2,6-dichlorophenylthioether;
N-(n-propyl), N-[α-(5-pyrimidyl)acetyl]ethanolamine 2,4,6-trichlorophenylether;
N-(n-propyl), N-[α-(5-pyrimidyl)acetyl]2-aminoethanethiol 2,4,6-trichlorophenylthioether;
N-ethyl, N-[α-(3-pyridyl)thioacetyl]ethanolamine phenylether;
N-ethyl, N-[α-(3-pyridyl)thioacetyl]2-aminoethanethiol phenylthioether;
N-(n-propyl), N-[α-(5-pyrimidyl)thioacetyl]ethanolamine 4-t-butylphenylether
N-(n-propyl), N-[α-(5-pyrimidyl)thioacetyl]2-aminoethanethiol 4-t-butylphenylthioether;
N-ethyl, N-[α-(1-imidazolyl)acetyl]ethanolamine 2,4,6-trichlorophenylether;
N-ethyl, N-[α-(1-imidazolyl)acetyl]2-aminoethanethiol 2,4,6-trichlorophenylthioether;
N-ethyl, N-[α-(3-pyrrolyl)acetyl]2-aminoethanethiol 2,4,6-tribromophenylthioether;
N-ethyl, N-[α-(3-pyrrolyl)acetyl]ethanolamine 2,4,6-tribromophenylether;
N-(n-propyl), N-[α-(2-pyrazinyl)acetyl]ethanolamine 2,4,6-trichlorophenylether;
N-(n-propyl), N-[α-(2-pyrazinyl)acetyl]2-aminoethanethiol 2,4,6-trichlorophenylthioether;
N-(n-propyl), N-[α-[6-(1,2,4-triazinyl)]acetyl ethanolamine 2,4,6-trichlorophenylether;
N-(n-propyl), N-[α-[6-(1,2,4-triazinyl)]acetyl 2-aminoethanethiol 2,4,6-trichlorophenylthioether;
N-(n-propyl), N-[α-[6-(1,2,4-triazinyl)]thioacetyl]ethanolamine 4-t-butylphenylether;
N-(n-propyl), N-[α-[6-(1,2,4-triazinyl)]thioacetyl]2-aminoethanethiol 2,4,6-trichlorophenylthioether;
N-(n-propyl), N-[α-[1-(1,2,4-triazolyl)]thioacetyl ethanolamine 2,4,6-trichlorophenylether;
N-(n-propyl), N-α-[1-(1,2,4-triazolyl)]acetyl 2-amino ethanethiol 2,6dichlorophenylthioether;
N-(n-propyl), N-[α-[1-(1,2,4-triazolyl)]thioacetyl]2-aminoethanethiol 2,6-dichlorophenylthioether; i5
N-(n-propyl), N-[β-(5-pyrimidyl)acrylyl]ethanolamine 2,4,6-trichlorophenylether;
N-(n-propyl), N-[β-(2-pyrazinyl)acrylyl]ethanolamine 2,4,6-trichlorophenylether;
N-(n-propyl), N-[β-[6-(1,2,4-triazinyl)]acrylyl]ethanolamine 2,4,6-trichlorophenylether;
N-(n-propyl), N-[β-(5-imidazolyl)acrylyl]ethanolamine 2,4,6-trichlorophenylether;
N-(n-propyl), N-[β-(3-pyrrolyl)acrylyl]ethanolamine 2,4,6-trichlorophenylether;
N-(n-propyl), N-[β-(3-pyrazolyl)acrylyl]ethanolamine 2,4,6-trichlorophenylether;
N-(n-propyl), N-[β-[3-(1,2,4-triazolyl)]acrylyl]ethanolamine 2,4,6-trichlorophenylether;
N-(n-propyl), N-[β-(3-pyridyl)thioacrylyl]ethanolamine 2,4,6-trichlorophenylether;
N-(n-propyl), N-[β-(3-pyridyl)thioacrylyl]2-aminoethanethiol 2,4,6-trichlorophenylthioether; and
N-(n-propyl), N-[β-(3-pyridyl)acrylyl]2-aminoethanethiol 2,4,6-trichlorophenylthioether.

Example A

Bean Powdery Mildew

The compounds of the invention were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F at night with daytime temperatures of 72° F to 80° F; relative humidity was maintained at 40% to 60%. The percent disease control provided by a given test compound was based on the percent disease reduction relative to the untreated check plants. The results are tabulated in Table II.

Example B

Tomato Late Blight

Compounds of the invention were tested for the preventative control of the Tomato Late Blight organism *Phytophthora infestans*. Five- to six-week-old tomato (cultivar Bonny Best) seedlings were used. The tomato plants were sprayed with a 250-ppm suspension of the test compound in acetone, water and a nonionic emulsifier. The sprayed plants were then inoculated 1 day later with the organism, placed in an environmental chamber and incubated at 66° F to 68° F and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

Example

Celery Late Blight

The Celery Late Blight tests were conducted using celery (Utah) plants 11 weeks old. The Celery Late Blight organism was *Septoria apii*. The celery plants were sprayed with 250-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given candidate toxicant is based on the percent disease reduction relative to untreated check plants. The results are reported in Table II.

Example D

Tomato Early Blight

Compounds of the invention were tested for the control of the Tomato Early Blight organism *Alternaria solani conidia*. Tomato (variety Bonny Best) seedings of 6- to 7-weeks old were used. The tomato plants were sprayed with a 250-ppm solution of the test compound in an acetone-and-water solution containing a small amount of a nonionic emulsifier. The sprayed plants were inoculated day later with the organism, placed in the environmental chamber and incubated at 66° F to 68° F. and 100% relative humidity for 24 hours. Following the incubation, the plants were maintained in a greenhouse for about 12 days. Percent disease control was based on the percent disease development on untreated check plants. The compounds

Example E

Grape Downy Mildew

The compounds of the invention were tested for the control of the Grape Downy Mildew organism *Plasmopara viticola*. Detached leaves, between 70 mm and 85 mm in diameter, 7-week-old *Vitis vinifera* cultivar Emperor grape seedlings were used as hosts. The leaves were sprayed with a 250-ppm solution of the test compound in acetone. The sprayed leaves were dried, inocultted with a spore suspension of the organism, placed in a humid environmental chamber and incubated at 66° F. to 68° F. and about 100% relative humidity. After incubation for 2 days, the plants were then held in a greenhouse 7 to 9 days; then the amount of disease control was determined. The percent disease control provided by a given test compound was based on the percent disease reduction relative to untreated check plants. The results are tabulated in Table II.

Example F

Leaf Rust

The Leaf Rust test was made using pinto beans. The pathogen was *Uromyces phaseoli tipica*. The pinto bean plants were sprayed with a 250-ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68° F to 70° F. The plants were then removed from the chamber, allowed to dry, and then maintained in a greenhouse at a 60% to 80% relative humidity. The rate of infection on the leaves was made after about 14 days. The percent disease control provided by a given test compound was based on the percent disease reduction relative to untreated check plants. The results are reported in Table II.

Example G

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 \times \left( \frac{\% \text{ disease in treated plants}}{\% \text{ disease in check}} \right)$$

The results are tabulated in Table II.

TABLE I

| Compound No. | Compound | ANALYSIS | | | | | | Form | m.p. |
|---|---|---|---|---|---|---|---|---|---|
| | | Carbon | | Hydrogen | | Nitrogen | | | |
| | | Calc. | Found | Calc. | Found | Calc. | Found | | |
| 1 | Cl-[2,4,6-trichlorophenyl]-OCH₂CH₂NCCH₂—N(imidazole), with CH₂CH₂CH₃ chain | 45.99 | 45.44 | 4.37 | 4.36 | 14.30 | 12.35 | oil | |
| 2 | Cl-[2,4,6-trichlorophenyl]-OCH₂CH₂NCCH=CH-(pyridyl), with CH₂CH₂CH₃ chain | 55.16 | 53.10 | 4.54 | 4.79 | 6.77 | 6.59 | oil | |
| 3 | Cl-[2,4,6-trichlorophenyl]-OCH₂CH₂NCCH₂Br, with CH₂CH₂CH₃ chain | 38.69 | 39.63 | 3.75 | 3.96 | 3.47 | 3.35 | oil | |

TABLE I-continued

| Compound No. | Compound | ANALYSIS | | | | | | Form | m.p. |
|---|---|---|---|---|---|---|---|---|---|
| | | Carbon | | Hydrogen | | Nitrogen | | | |
| | | Calc. | Found | Calc. | Found | Calc. | Found | | |
| 4 | 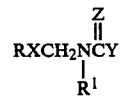 | 53.82 | 52.81 | 4.73 | 5.18 | 6.98 | 6.83 | oil | |

TABLE II

| Compound No. | Fungicidal Activity % Control | | | | | | |
|---|---|---|---|---|---|---|---|
| | GDM | TLB | CLB | TEB | BR | BPM | RB |
| 1 | 10 | 10 | 33 | 91 | 0 | 97 | 0 |
| 2 | 23 | 56 | 40 | 15 | 11 | 46 | 0 |
| 3 | 30 | 20 | 94 | 31 | 0 | 0 | 88 |
| 4 | 11 | 11 | 7 | 19 | 0 | 91 | 10 |

GDM - Grape Downy Mildew (*Plasmopara viticola*)
TLB - Tomato Late Blight (*Phytophthora infestans*)
CLB - Celery Late Blight (*Septoria apii*)
TEB - Tomato Early Blight (*Alternaria solani conidia*)
BR - Bean Rust (*Uromyces phaseoli tipica*)
BPM - Bean Powdery Mildew (*Erysiphe polygoni*)
RB - Rice Blast (*Piricularia oryzae*)

We claim:

1. A compound of the formula:

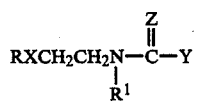

wherein R is phenyl or phenyl substituted with 1 to 4 substituents independently selected from fluoro, chloro, bromo, iodo, lower alkyl and trihalomethyl; $R^1$ is lower alkyl; Y is $-CH_2W$ where W is a 5- or 6-membered aromatic heterocyclic ring containing 2 or 3 nitrogen atoms and the remainder of the ring atoms carbon atoms; Z is oxygen or sulfur and X is oxygen or sulfur.

2. A compound of the formula defined in claim 1 wherein Y is 1-(1,2,4-triazolyl) methyl.
3. A compound of the formula defined in claim 2 wherein R is 2,4,6-trihalophenyl.
4. A compound of the formula defined in claim 1 wherein R is 2,4,6-trichlorophenyl.
5. A compound of the formula defined in claim 4 wherein X is oxygen.
6. A compound of the formula defined in claim 5 wherein $R^1$ is n-propyl.
7. A compound according to claim 1 wherein W is imidazolyl, pyrazolyl, 1,2,4-trizolyl, pyridazinyl, pyrimidyl, pyrazinyl or 1,2,4-triazinyl.
8. A compound of the formula

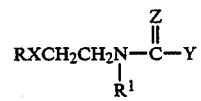

wherein Y is 1-(1,2,4-triazolyl) methyl, R is 2,4,6-trichlorophenyl, X is oxygen, and $R^1$ is n-propyl and Z is oxygen or sulfur.

9. A fungicidal composition comprising a biologically inert carrier and a fungicidally effective amount of a compound of the formula defined in claim 1.
10. A fungicidal composition comprising a biologically inert carrier and a fungicidally effective amount of a compound of the formula defined in claim 8.
11. A method for controlling fungi comprising contacting said fungi or their growth environment with a fungicidally effective amount of a compound of the formula defined in claim 1.
12. A method for controlling fungi comprising contacting said fungi or their growth environment with a fungicidally effective amount of a compound of the formula defined in claim 8.
13. A fungicidal composition comprising a biologically inert carrier and a fungicidally effective amount of a compound of the formula defined in claim 7.
14. A method for controlling fungi comprising contacting said fungi or their growth environment with a fungicidally effective amount of a compound of the formula defined in claim 7.
15. A compound of the formula:

$$RXCH_2CH_2N(R^1)-\overset{Z}{\underset{}{C}}-Y$$

wherein R is phenyl or phenyl substituted with 1 to 4 substituents independently selected from fluoro, chloro, bromo, iodo, and lower alkyl; $R^1$ is lower alkyl; Y is $-CH^2W$ where W is imidazolyl or 1,2,4-triazolyl, both attached at the ring nitrogen; Z is oxygen or sulfur and X is oxygen or sulfur.

16. A fungicidal composition comprising a biologically inert carrier and a fungicidally effective amount of a compound of the formula defined in claim 15.
17. A method for controlling fungi comprising contacting said fungi or their growth environment with a fungicidally effective amount of a compound of the formula defined in claim 15.

* * * * *